(12) United States Patent
Kase et al.

(10) Patent No.: US 8,034,820 B2
(45) Date of Patent: Oct. 11, 2011

(54) PHARMACEUTICAL COMPOSITION

(75) Inventors: Hiroshi Kase, Tokyo (JP); Minoru Kobayashi, Sunto-gun (JP); Shizuo Shiozaki, Fuji (JP); Akihisa Mori, Narashino (JP); Naoki Seno, Moriya (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 1224 days.

(21) Appl. No.: 10/565,239

(22) PCT Filed: Jul. 22, 2004

(86) PCT No.: PCT/JP2004/010758
§ 371 (c)(1),
(2), (4) Date: Jan. 19, 2006

(87) PCT Pub. No.: WO2005/009444
PCT Pub. Date: Feb. 3, 2005

(65) Prior Publication Data
US 2006/0241102 A1    Oct. 26, 2006

(30) Foreign Application Priority Data

Jul. 25, 2003   (JP) ................................. 2003-201549

(51) Int. Cl.
| | |
|---|---|
| *A01N 43/90* | (2006.01) |
| *A01N 43/52* | (2006.01) |
| *A61K 31/522* | (2006.01) |
| *A61K 31/415* | (2006.01) |
| *C07D 473/00* | (2006.01) |
| *C07D 403/02* | (2006.01) |
| *C07D 317/44* | (2006.01) |
| *C07C 211/00* | (2006.01) |
| *C07C 213/00* | (2006.01) |
| *C07C 215/00* | (2006.01) |
| *C07C 217/00* | (2006.01) |

(52) U.S. Cl. ................... 514/263.34; 514/394; 544/267; 548/303.4; 549/437; 564/336; 564/347

(58) Field of Classification Search .................. 514/263, 514/263.34, 394; 544/267; 548/303.4; 549/437; 564/336, 347
See application file for complete search history.

(56) References Cited

U.S. PATENT DOCUMENTS

| | | | |
|---|---|---|---|
| 6,727,259 B2 * | 4/2004 | Shimada et al. | 514/263.34 |
| 6,875,772 B2 | 4/2005 | Neustadt et al. | |
| 7,078,408 B2 | 7/2006 | Neustadt et al. | |
| 2003/0191130 A1 | 10/2003 | Neustadt et al. | |
| 2004/0198753 A1 | 10/2004 | Kase et al. | |
| 2005/0113380 A1 | 5/2005 | Neustadt et al. | |
| 2006/0148827 A1 | 7/2006 | Kase et al. | |
| 2006/0178379 A1 | 8/2006 | Kase et al. | |

FOREIGN PATENT DOCUMENTS

| | | |
|---|---|---|
| JP | 2928386 | 5/1999 |
| WO | WO 03/022283 | 3/2003 |

OTHER PUBLICATIONS

Kanda, et al., "Combined use of the Adenosine A2A Antagonist KW-6002 with L-DOPA or with selective D1 or D2 Dopamine Agonists Increases Antiparkinsonian Activity but Not Dyskinesia in MPTP-Treated Monkeys," Exp. Neurology, vol. 162 (2000) 321-27.
Petzer, et al., "Inhibition of Monoamine Oxidase B by Selective Adenosine A2A Receptor Antagonists," Bioorganic & Med. Chem., vol. 11 (2003) 1299-310.

* cited by examiner

*Primary Examiner* — Sreeni Padmanabhan
*Assistant Examiner* — Sarah Pihonak
(74) *Attorney, Agent, or Firm* — Fitzpatrick, Cella, Harper & Scinto

(57) ABSTRACT

The present invention provides pharmaceutical compositions, which are useful for treatment of depression and the like, and which comprises a compound having an adenosine $A_{2A}$ receptor antagonistic activity such as (E)-8-(3,4-dimethoxystyryl)-1,3-diethyl-7-methyl-3,7-dihydro-1H-purine-2,6-dione or a pharmaceutically acceptable salt thereof and an antidepressant drug (for example, a tricyclic antidepressant, a tetracyclic antidepressant, a selective serotonin reuptake inhibitor, a selective noradrenalin reuptake inhibitor, a dopamine reuptake inhibitor, a serotonin-noradrenalin reuptake inhibitor, a monoamine oxidase inhibitor, a 5-$HT_2$ antagonist or the like), and the like.

9 Claims, No Drawings

PHARMACEUTICAL COMPOSITION

TECHNICAL FIELD

The present invention relates to pharmaceutical compositions which comprise a compound having an adenosine $A_{2A}$ receptor antagonistic activity and an antidepressant drug, and the like.

BACKGROUND ART (E)-8-(3,4-dimethoxystyryl)-1,3-diethyl-7-methyl-3,7-dihydro-1H-purine-2,6-dione or a pharmaceutically acceptable salt thereof are known to show an adenosine $A_{2A}$ receptor antagonistic activity and be useful as a therapeutic agent for depression and the like (Japanese Patent No. 2928386).

Furthermore, pharmaceutical compositions which comprise a non-xanthine derivative having an adenosine $A_{2A}$ receptor antagonistic activity and an antidepressant drug are known (WO 03/022283).

On the other hand, a treatment of depression carried out by an administration of a tricyclic antidepressant, a tetracyclic antidepressant, a selective serotonin reuptake inhibitor, a selective noradrenalin reuptake inhibitor, a dopamine reuptake inhibitor, a serotonin-noradrenalin reuptake inhibitor or the like, or by an administration in combination of these. However, these administrations involve medical problems of side effects such as side effects on an autonomic nervous system, cardiotoxicity, side effects on a digestive system (for example, nausea, anorexia, loose stool, diarrhea and the like), sexual dysfunctions, withdrawal syndrome, extrapyramidal disorders, serotonin syndrome, weight loss, anxiety and impatience, syndrome of inappropriate antidiuretic hormone in the aged, urinary retention, dysuria, a rash, headache and palpitation [Pharmacia, 38, 737-742, (2001)]. Furthermore, treatment of depression is carried out by an administration of a monoamine oxidase inhibitor. However, the administration also involves medical problems of side effects such as serious hepatic function disorder and rise of blood pressure [Pharmacia, 38, 737-742 (2001)].

DISCLOSURE OF THE INVENTION

An object of the present invention is to provide pharmaceutical compositions which comprise (E)-8-(3,4-dimethoxystyryl)-1,3-diethyl-7-methyl-3,7-dihydro-1H-purine-2,6-dione or a pharmaceutically acceptable salt thereof and an antidepressant drug, and the like.

The invention relates to the following items (1) to (118).

(1) A pharmaceutical composition which comprises
(a) (E)-8-(3,4-dimethoxystyryl)-1,3-diethyl-7-methyl-3,7-dihydro-1H-purine-2,6-dione represented by the formula (I):

(I)

or a pharmaceutically acceptable salt thereof, and
(b) an antidepressant drug.

(2) A pharmaceutical composition which comprises (E)-8-(3,4-dimethoxystyryl)-1,3-diethyl-7-methyl-3,7-dihydro-1H-purine-2,6-dione represented by the formula (I):

(I)

or a pharmaceutically acceptable salt thereof
for administering simultaneously or separately at a time interval in combination with an antidepressant drug.

(3) The pharmaceutical composition according to the above (1) or (2), wherein the antidepressant drug is a tricyclic antidepressant, a tetracyclic antidepressant, a selective serotonin reuptake inhibitor, a selective noradrenalin reuptake inhibitor, a dopamine reuptake inhibitor, a serotonin-noradrenalin reuptake inhibitor, a monoamine oxidase inhibitor or a serotonin 2 (5-HT$_2$) antagonist.

(4) The pharmaceutical composition according to the above (1) or (2), wherein the antidepressant drug is a tricyclic antidepressant.

(5) The pharmaceutical composition according to the above (4), wherein the tricyclic antidepressant is imipramine hydrochloride, clomipramine hydrochloride, amitriptyline hydrochloride, nortriptyline hydrochloride, amoxapine, trimipramine maleate, lofepramine, lofepramine hydrochloride, dosulepin hydrochloride, protriptyline, doxepin or desipramine hydrochloride.

(6) The pharmaceutical composition according to the above (1) or (2), wherein the antidepressant drug is a tetracyclic antidepressant.

(7) The pharmaceutical composition according to the above (6), wherein the tetracyclic antidepressant is maprotiline hydrochloride, mianserin hydrochloride or setiptiline maleate.

(8) The pharmaceutical composition according to the above (1) or (2), wherein the antidepressant drug is a selective serotonin reuptake inhibitor.

(9) The pharmaceutical composition according to the above (8), wherein the selective serotonin reuptake inhibitor is fluoxetine hydrochloride, sertraline hydrochloride, paroxetine hydrochloride, paroxetine hydrochloride hydrate, citalopram hydrobromide, fluvoxamine maleate, trazodone hydrochloride or nefazodone hydrochloride.

(10) The pharmaceutical composition according to the above (1) or (2), wherein the antidepressant drug is a selective noradrenalin reuptake inhibitor.

(11) The pharmaceutical composition according to the above (10), wherein the selective noradrenalin reuptake inhibitor is reboxetine mesylate, mirtazapine, maprotiline hydrochloride, nortriptyline hydrochloride, amoxapine, bupropion or bupropion hydrochloride.

(12) The pharmaceutical composition according to the above (1) or (2), wherein the antidepressant drug is a serotonin-noradrenalin reuptake inhibitor.

(13) The pharmaceutical composition according to the above (12), wherein the serotonin-noradrenalin reuptake inhibitor is milnacipran hydrochloride, venlafaxine hydrochloride or duloxetine hydrochloride.

(14) The pharmaceutical composition according to the above (1) or (2), wherein the antidepressant drug is a dopamine reuptake inhibitor.

(15) The pharmaceutical composition according to the above (14), wherein the dopamine reuptake inhibitor is venlafaxine hydrochloride.

(16) The pharmaceutical composition according to the above (1) or (2), wherein the antidepressant drug is a monoamine oxidase inhibitor.

(17) The pharmaceutical composition according to the above (16), wherein the monoamine oxidase inhibitor is selegiline hydrochloride, safinamide mesylate or moclobemide.

(18) The pharmaceutical composition according to the above (1) or (2), wherein the antidepressant drug is a 5-HT$_2$ antagonist.

(19) The pharmaceutical composition according to the above (18), wherein the 5-HT$_2$ antagonist is mirtazapine, trazodone hydrochloride or nefazodone hydrochloride.

(20) A therapeutic agent for depression which comprises (a) (E)-8-(3,4-dimethoxystyryl)-1,3-diethyl-7-methyl-3,7-dihydro-1H-purine-2,6-dione represented by the formula (I):

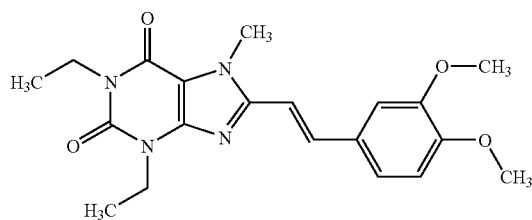

(I)

or a pharmaceutically acceptable salt thereof and
(b) an antidepressant drug for administering simultaneously or separately at a time interval.

(21) The therapeutic agent for depression according to the above (20), wherein the antidepressant drug is a tricyclic antidepressant, a tetracyclic antidepressant, a selective serotonin reuptake inhibitor, a selective noradrenalin reuptake inhibitor, a dopamine reuptake inhibitor, a serotonin-noradrenalin reuptake inhibitor, a monoamine oxidase inhibitor or a 5-HT$_2$ antagonist.

(22) The therapeutic agent for depression according to the above (20), wherein the antidepressant drug is a tricyclic antidepressant.

(23) The therapeutic agent for depression according to the above (22), wherein the tricyclic antidepressant is imipramine hydrochloride, clomipramine hydrochloride, amitriptyline hydrochloride, nortriptyline hydrochloride, amoxapine, trimipramine maleate, lofepramine, lofepramine hydrochloride, dosulepin hydrochloride, protriptyline, doxepin or desipramine hydrochloride.

(24) The therapeutic agent for depression according to the above (20), wherein the antidepressant drug is a tetracyclic antidepressant.

(25) The therapeutic agent for depression according to the above (24), wherein the tetracyclic antidepressant is maprotiline hydrochloride, mianserin hydrochloride or setiptiline maleate.

(26) The therapeutic agent for depression according to the above (20), wherein the antidepressant drug is a selective serotonin reuptake inhibitor.

(27) The therapeutic agent for depression according to the above (26), wherein the selective serotonin reuptake inhibitor is fluoxetine hydrochloride, sertraline hydrochloride, paroxetine hydrochloride, paroxetine hydrochloride hydrate, citalopram hydrobromide, fluvoxamine maleate, trazodone hydrochloride or nefazodone hydrochloride.

(28) The therapeutic agent for depression according to the above (20), wherein the antidepressant drug is a selective noradrenalin reuptake inhibitor.

(29) The therapeutic agent for depression according to the above (28), wherein the selective noradrenalin reuptake inhibitor is reboxetine mesylate, mirtazapine, maprotiline hydrochloride, nortriptyline hydrochloride, amoxapine, bupropion or bupropion hydrochloride.

(30) The therapeutic agent for depression according to the above (20), wherein the antidepressant drug is a serotonin-noradrenalin reuptake inhibitor.

(31) The therapeutic agent for depression according to the above (30), wherein the serotonin-noradrenalin reuptake inhibitor is milnacipran hydrochloride, venlafaxine hydrochloride or duloxetine hydrochloride.

(32) The therapeutic agent for depression according to the above (20), wherein the antidepressant drug is a dopamine reuptake inhibitor.

(33) The therapeutic agent for depression according to the above (32), wherein the dopamine reuptake inhibitor is venlafaxine hydrochloride.

(34) The therapeutic agent for depression according to the above (20), wherein the antidepressant drug is a monoamine oxidase inhibitor.

(35) The therapeutic agent for depression according to the above (34), wherein the monoamine oxidase inhibitor is selegiline hydrochloride, safinamide mesylate or moclobemide.

(36) The therapeutic agent for depression according to the above (20), wherein the antidepressant drug is a 5-HT$_2$ antagonist.

(37) The therapeutic agent for depression according to the above (36), wherein the 5-HT$_2$ antagonist is mirtazapine, trazodone hydrochloride or nefazodone hydrochloride.

(38) (E)-8-(3,4-dimethoxystyryl)-1,3-diethyl-7-methyl-3,7-dihydro-1H-purine-2,6-dione represented by the formula (I):

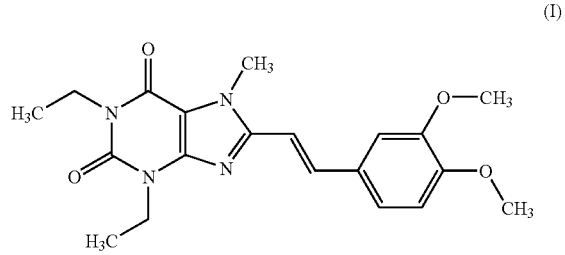

(I)

or a pharmaceutically acceptable salt thereof
for administering simultaneously or separately at a time interval in combination with an antidepressant drug.

(39) The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a tricyclic antidepressant, a tetracyclic antidepressant, a selective a serotonin reuptake inhibitor, a selective noradrenalin reuptake inhibitor, a dopamine reuptake inhibitor, a serotonin-noradrenalin reuptake inhibitor, a monoamine oxidase inhibitor or a 5-HT$_2$ antagonist.

(40) The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a tricyclic antidepressant.

(41) The (E)-8-(3,4-dimethoxystyryl)-1,3-diethyl-7-methyl-3,7-dihydro-1H-purine-2,6-dione or a pharmaceutically acceptable salt thereof according to the above (40), wherein the tricyclic antidepressant is imipramine hydrochloride, clomipramine hydrochloride, amitriptyline hydrochloride, nortriptyline hydrochloride, amoxapine, trimipramine maleate, lofepramine, lofepramine hydrochloride, dosulepin hydrochloride, protriptyline, doxepin or desipramine hydrochloride.

(42) The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a tetracyclic antidepressant.

(43) The (E)-8-(3,4-dimethoxystyryl)-1,3-diethyl-7-methyl-3,7-dihydro-1H-purine-2,6-dione or a pharmaceutically acceptable salt thereof according to the above (42), wherein the tetracyclic antidepressant is maprotiline hydrochloride, mianserin hydrochloride or setiptiline maleate.

(44) The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a selective serotonin reuptake inhibitor.

(45) The (E)-8-(3,4-dimethoxystyryl)-1,3-diethyl-7-methyl-3,7-dihydro-1H-purine-2,6-dione or a pharmaceutically acceptable salt thereof according to the above (44), wherein the selective serotonin reuptake inhibitor is fluoxetine hydrochloride, sertraline hydrochloride, paroxetine hydrochloride, paroxetine hydrochloride hydrate, citalopram hydrobromide, fluvoxamine maleate, trazodone hydrochloride or nefazodone hydrochloride.

(46) The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a selective noradrenalin reuptake inhibitor.

(47) The (E)-8-(3,4-dimethoxystyryl)-1,3-diethyl-7-methyl-3,7-dihydro-1H-purine-2,6-dione or a pharmaceutically acceptable salt thereof according to the above (46), wherein the selective noradrenalin reuptake inhibitor is reboxetine mesylate, mirtazapine, maprotiline hydrochloride, nortriptyline hydrochloride, amoxapine, bupropion or bupropion hydrochloride.

(48) The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a serotonin-noradrenalin reuptake inhibitor.

(49) The (E)-8-(3,4-dimethoxystyryl)-1,3-diethyl-7-methyl-3,7-dihydro-1H-purine-2,6-dione or a pharmaceutically acceptable salt thereof according to the above (48), wherein the serotonin-noradrenalin reuptake inhibitor is milnacipran hydrochloride, venlafaxine hydrochloride or duloxetine hydrochloride.

(50) The (E)-8-(3,4-dimethoxystyryl)-1,3-diethyl-7-methyl-3,17-dihydro-1H-purine-2,6-dione or a pharmaceutically acceptable salt thereof according to the above (38), wherein the antidepressant drug is a dopamine reuptake inhibitor.

(51) The (E)-8-(3,4-dimethoxystyryl)-1,3-diethyl-7-methyl-3,7-dihydro-1H-purine-2,6-dione or a pharmaceutically acceptable salt thereof according to the above (50), wherein the dopamine reuptake inhibitor is venlafaxine hydrochloride.

(52). The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a monoamine oxidase inhibitor.

(53) The (E)-8-(3,4-dimethoxystyryl)-1,3-diethyl-7-methyl-3,7-dihydro-1H-purine-2,6-dione or a pharmaceutically acceptable salt thereof according to the above (52), wherein the monoamine oxidase inhibitor is selegiline hydrochloride, safinamide mesylate or moclobemide.

(54) The (E)-8-(3,4-dimethoxystyryl)-1,3-diethyl-7-methyl-3,7-dihydro-1H-purine-2,6-dione or a pharmaceutically acceptable salt thereof according to the above (38), wherein the antidepressant drug is a 5-$HT_2$ antagonist.

(55) The (E)-8-(3,4-dimethoxystyryl)-1,3-diethyl-7-methyl-3,7-dihydro-1H-purine-2,6-dione or a pharmaceutically acceptable salt thereof according to the above (54), wherein the 5-$HT_2$ antagonist is mirtazapine, trazodone hydrochloride or nefazodone hydrochloride.

(56) A kit which comprises (a) a first component comprising (E)-8-(3,4-dimethoxystyryl)-1,3-diethyl-7-methyl-3,7-dihydro-1H-purine-2,6-dione represented by the formula (I):

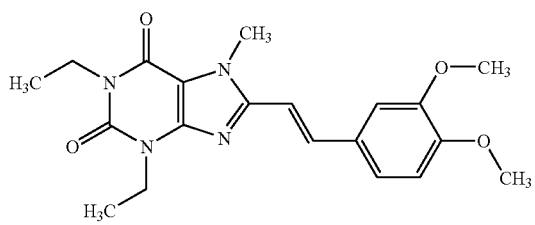

(I)

or a pharmaceutically acceptable salt thereof and (b) a second component comprising an antidepressant drug.

(57) A kit for treatment of depression which comprises (a) a first component comprising (E)-8-(3,4-dimethoxystyryl)-1,3-diethyl-7-methyl-3,7-dihydro-1H-purine-2,6-dione represented by the formula (I):

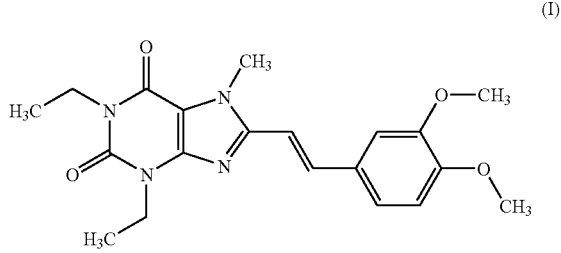

(I)

or a pharmaceutically acceptable salt thereof and (b) a second component comprising an antidepressant drug.

(58) The kit according to the above (56) or (57), wherein the antidepressant drug is a tricyclic antidepressant, a tetracyclic antidepressant, a selective serotonin reuptake inhibitor, a selective noradrenalin reuptake inhibitor, a dopamine reuptake inhibitor, a serotonin-noradrenalin reuptake inhibitor, a monoamine oxidase inhibitor or a 5-$HT_2$ antagonist.

(59) The kit according to the above (56) or (57), wherein the antidepressant drug is a tricyclic antidepressant.

(60) The kit according to the above (59), wherein the tricyclic antidepressant is imipramine hydrochloride, clomipramine hydrochloride, amitriptyline hydrochloride, nortriptyline hydrochloride, amoxapine, trimipramine maleate, lofepramine, lofepramine hydrochloride, dosulepin hydrochloride, protriptyline, doxepin or desipramine hydrochloride.

(61) The kit according to the above (56) or (57), wherein the antidepressant drug is a tetracyclic antidepressant.

(62) The kit according to the above (61), wherein the tetracyclic antidepressant is maprotiline hydrochloride, mianserin hydrochloride or setiptiline maleate.

(63) The kit according to the above (56) or (57), wherein the antidepressant drug is a selective serotonin reuptake inhibitor.

(64) The kit according to the above (63), wherein the selective serotonin reuptake inhibitor is fluoxetine hydrochloride, sertraline hydrochloride, paroxetine hydrochloride, paroxetine hydrochloride hydrate, citalopram hydrobromide, fluvoxamine maleate, trazodone hydrochloride or nefazodone hydrochloride.

(65) The kit according to the above (56) or (57), wherein the antidepressant drug is a selective noradrenalin reuptake inhibitor.

(66) The kit according to the above (65), wherein the selective noradrenalin reuptake inhibitor is reboxetine mesylate, mirtazapine, maprotiline hydrochloride, nortriptyline hydrochloride, amoxapine, bupropion or bupropion hydrochloride.

(67) The kit according to the above (56) or (57), wherein the antidepressant drug is a serotonin-noradrenalin reuptake inhibitor.

(68) The kit according to the above (67), wherein the serotonin-noradrenalin reuptake inhibitor is milnacipran hydrochloride, venlafaxine hydrochloride or duloxetine hydrochloride.

(69) The kit according to the above (56) or (57), wherein the antidepressant drug is a dopamine reuptake inhibitor.

(70) The kit according to the above (69), wherein the dopamine reuptake inhibitor is venlafaxine hydrochloride.

(71) The kit according to the above (56) or (57), wherein the antidepressant drug is a monoamine oxidase inhibitor.

(72) The kit according to the above (71), wherein the monoamine oxidase inhibitor is selegiline hydrochloride, safinamide mesylate or moclobemide.

(73) The kit according to the above (56) or (57), wherein the antidepressant drug is a 5-HT$_2$ antagonist.

(74) The kit according to the above (73), wherein the 5-HT$_2$ antagonist is mirtazapine, trazodone hydrochloride or nefazodone hydrochloride.

(75) A method for treating depression, which comprises administering
(a) (E)-8-(3,4-dimethoxystyryl)-1,3-diethyl-7-methyl-3,7-dihydro-1H-purine-2,6-dione represented by the formula (I):

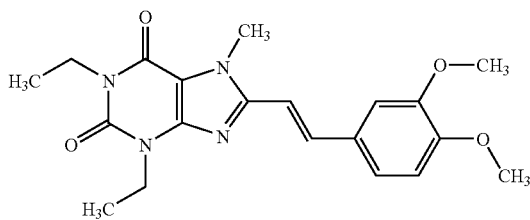

or a pharmaceutically acceptable salt thereof and
(b) an antidepressant drug
simultaneously or separately at a time interval.

(76) The method for treating depression according to the above (75), wherein the antidepressant drug is a tricyclic antidepressant, a tetracyclic antidepressant, a selective serotonin reuptake inhibitor, a selective noradrenalin reuptake inhibitor, a dopamine reuptake inhibitor, a serotonin-noradrenalin reuptake inhibitor, a monoamine oxidase inhibitor or a 5-HT$_2$ antagonist.

(77) The method for treating depression according to the above (75), wherein the antidepressant drug is a tricyclic antidepressant.

(78) The method for treating depression according to the above (77), wherein the tricyclic antidepressant is imipramine hydrochloride, clomipramine hydrochloride, amitriptyline hydrochloride, nortriptyline hydrochloride, amoxapine, trimipramine maleate, lofepramine, lofepramine hydrochloride, dosulepin hydrochloride, protriptyline, doxepin or desipramine hydrochloride.

(79) The method for treating depression according to the above (75), wherein the antidepressant drug is a tetracyclic antidepressant.

(80) The method for treating depression according to the above (79), wherein the tetracyclic antidepressant is maprotiline hydrochloride, mianserin hydrochloride or setiptiline maleate.

(81) The method for treating depression according to the above (75), wherein the antidepressant drug is a selective serotonin reuptake inhibitor.

(82) The method for treating depression according to the above (81), wherein the selective serotonin reuptake inhibitor is fluoxetine hydrochloride, sertraline hydrochloride, paroxetine hydrochloride, paroxetine hydrochloride hydrate, citalopram hydrobromide, fluvoxamine maleate, trazodone hydrochloride or nefazodone hydrochloride.

(83) The method for treating depression according to the above (75), wherein the antidepressant drug is a selective noradrenalin reuptake inhibitor.

(84) The method for treating depression according to the above (83), wherein the selective noradrenalin reuptake inhibitor is reboxetine mesylate, mirtazapine, maprotiline hydrochloride, nortriptyline hydrochloride, amoxapine, bupropion or bupropion hydrochloride.

(85) The method for treating depression according to the above (75), wherein the antidepressant drug is a serotonin-noradrenalin reuptake inhibitor.

(86) The method for treating depression according to the above (85), wherein the serotonin-noradrenalin reuptake inhibitor is milnacipran hydrochloride, venlafaxine hydrochloride or duloxetine hydrochloride.

(87) The method for treating depression according to the above (75), wherein the antidepressant drug is a dopamine reuptake inhibitor.

(88) The method for treating depression according to the above (87), wherein the dopamine reuptake inhibitor is venlafaxine hydrochloride.

(89) The method for treating depression according to the above (75), wherein the antidepressant drug is a monoamine oxidase inhibitor.

(90) The method for treating depression according to the above (89), wherein the monoamine oxidase inhibitor is selegiline hydrochloride, safinamide mesylate or moclobemide.

(91) The method for treating depression according to the above (75), wherein the antidepressant drug is a 5-HT$_2$ antagonist.

(92) The method for treating depression according to the above (91), wherein the 5-HT$_2$ antagonist is mirtazapine, trazodone hydrochloride or nefazodone hydrochloride.

(93) A pharmaceutical composition which comprises
(a) a compound having an adenosine A$_{2A}$ receptor antagonistic activity or a pharmaceutically acceptable salt thereof and
(b) a monoamine oxidase inhibitor.

(94) A compound having an adenosine $A_{2A}$ receptor antagonistic activity or a pharmaceutically acceptable salt thereof for administering simultaneously or separately at a time interval in combination with a monoamine oxidase inhibitor.

(95) A pharmaceutical composition which comprises a compound having an adenosine $A_{2A}$ receptor antagonistic activity or a pharmaceutically acceptable salt thereof for administering simultaneously or separately at a time interval in combination with a monoamine oxidase inhibitor.

(96) A therapeutic agent for depression which comprises (a) a compound having an adenosine $A_{2A}$ receptor antagonistic activity or a pharmaceutically acceptable salt thereof and (b) a monoamine oxidase inhibitor for administering simultaneously or separately at a time interval.

(97) A kit which comprises
(a) a first component comprising a compound having an adenosine $A_{2A}$ receptor antagonistic activity or a pharmaceutically acceptable salt thereof and
(b) a second component comprising a monoamine oxidase inhibitor.

(98) A kit for treatment of depression which comprises
(a) a first component comprising a compound having an adenosine $A_{2A}$ receptor antagonistic activity or a pharmaceutically acceptable salt thereof and
(b) a second component comprising a monoamine oxidase inhibitor.

(99) A method for treating depression, which comprises administering
(a) a compound having an adenosine $A_{2A}$ receptor antagonistic activity or a pharmaceutically acceptable salt thereof and
(b) a monoamine oxidase inhibitor simultaneously or separately at a time interval.

(100) Use of a combination of
(a) a compound having an adenosine $A_{2A}$ receptor antagonistic activity or a pharmaceutically acceptable salt thereof and
(b) a monoamine oxidase inhibitor
for the manufacture of a therapeutic agent for depression.

(101) Use of a combination of
(a) (E)-8-(3,4-dimethoxystyryl)-1,3-diethyl-7-methyl-3,7-dihydro-1H-purine-2,6-dione represented by the formula (I):

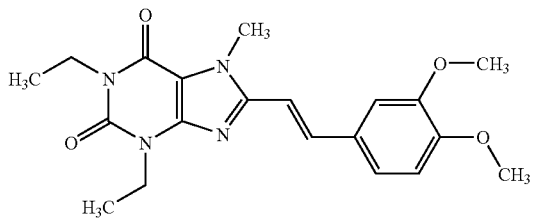

(I)

or a pharmaceutically acceptable salt thereof and
(b) an antidepressant drug for the manufacture of a therapeutic agent for depression.

(102) The use according to the above (101), wherein the antidepressant drug is a tricyclic antidepressant, a tetracyclic antidepressant, a selective serotonin reuptake inhibitor, a selective noradrenalin reuptake inhibitor, a dopamine reuptake inhibitor, a serotonin-noradrenalin reuptake inhibitor, a monoamine oxidase inhibitor or a 5-HT$_2$ antagonist.

(103) The use according to the above (101), wherein the antidepressant drug is a tricyclic antidepressant.

(104) The use according to the above (103), wherein the tricyclic antidepressant is imipramine hydrochloride, clomipramine hydrochloride, amitriptyline hydrochloride, nortriptyline hydrochloride, amoxapine, trimipramine maleate, lofepramine, lofepramine hydrochloride, dosulepin hydrochloride, protriptyline, doxepin or desipramine hydrochloride.

(105) The use according to the above (101), wherein the antidepressant drug is a tetracyclic antidepressant.

(106) The use according to the above (105), wherein the tetracyclic antidepressant is maprotiline hydrochloride, mianserin hydrochloride or setiptiline maleate.

(107) The use according to the above (101), wherein the antidepressant drug is a selective serotonin reuptake inhibitor.

(108) The use according to the above (107), wherein the selective serotonin reuptake inhibitor is fluoxetine hydrochloride, sertraline hydrochloride, paroxetine hydrochloride, paroxetine hydrochloride hydrate, citalopram hydrobromide, fluvoxamine maleate, trazodone hydrochloride or nefazodone hydrochloride.

(109) The use according to the above (101), wherein the antidepressant drug is a selective noradrenalin reuptake inhibitor.

(110) The use according to the above (109), wherein the selective noradrenalin reuptake inhibitor is reboxetine mesylate, mirtazapine, maprotiline hydrochloride, nortriptyline hydrochloride, amoxapine, bupropion or bupropion hydrochloride.

(111) The use according to the above (101), wherein the antidepressant drug is a serotonin-noradrenalin reuptake inhibitor.

(112) The use according to the above (111), wherein the serotonin-noradrenalin reuptake inhibitor is milnacipran hydrochloride, venlafaxine hydrochloride or duloxetine hydrochloride.

(113) The use according to the above (101), wherein the antidepressant drug is a dopamine reuptake inhibitor.

(114) The use according to the above (112), wherein the dopamine reuptake inhibitor is venlafaxine hydrochloride.

(115) The use according to the above (101), wherein the antidepressant drug is a monoamine oxidase inhibitor.

(116) The use according to the above (115), wherein the monoamine oxidase inhibitor is selegiline hydrochloride, safinamide mesylate or moclobemide.

(117) The use according to the above (101), wherein the antidepressant drug is a 5-HT$_2$ antagonist.

(118) The use according to the above (117), wherein the 5-HT$_2$ antagonist is mirtazapine, trazodone hydrochloride or nefazodone hydrochloride.

Hereinafter, (E)-8-(3,4-dimethoxystyryl)-1,3-diethyl-7-methyl-3,7-dihydro-1H-purine-2,6-dione represented by the formula (I):

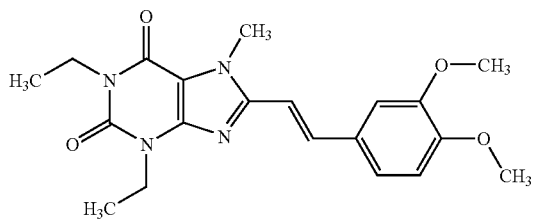

(I)

is referred to as Compound (I).
Examples of the pharmaceutically acceptable salt of Compound (I) include pharmaceutically acceptable acid addition salts. Specifically, inorganic acid addition salts such as hydrochloride, sulfate, hydrobromide, nitrate and phosphate, organic acid addition salts such as acetate, mesylate, succinate, maleate, fumarate, citrate and tartrate are included.

Although a method for production of Compound (I) is not particularly limited, Compound (I) can be obtained by any methods described in, for example, Japanese Pubilished Unexamined Patent Application No. 211856/94, EP 0590919, Japanese Published Unexamined Patent Application No. 040652/97 or the like, or modified methods thereof. The desired compound in each method of production can be isolated and purified by subjecting them to purification methods which are generally used in synthetic organic chemistry such as filtration, extraction, washing, drying, concentration, recrystallization and various types of chromatography.

When it is desired to obtain a salt of Compound (I), in instances in which Compound (I) is obtained in the form of a salt, the product may be directly purified. Alternatively, in instances in which Compound (I) is obtained in the form of a free base, the product may be dissolved or suspended in a suitable solvent, followed by addition of an acid or the like to form a salt.

Furthermore, Compound (I) and the pharmaceutically acceptable salt thereof may exist in the form of an adduct with water or various solvents. These adducts can also be used for the pharmaceutical composition, the therapeutic agent for depression, the kit, the kit for treatment of depression or the method for treating depression of the present invention, and are included in the (E)-8-(3,4-dimethoxystyryl)-1,3-diethyl-7-methyl-3,7-dihydro-1H-purine-2,6-dione or a pharmaceutically acceptable salt thereof of the present invention.

Although the compound having an adenosine $A_{2A}$ receptor antagonistic activity is not particularly limited, as long as it is a compound having an adenosine $A_{2A}$ receptor antagonistic activity, examples of the compound having an adenosine $A_{2A}$ receptor antagonistic activity include compounds described in, Japanese Patent No. 2928386, WO01/92264, U.S. Pat. No. 5,565,460, U.S. Pat. No. 5,587,378, U.S. Pat. No. 5,543,415, EP1016407, WO01/17999, WO01/62233, WO01/97786, WO01/92264, WO01/13681, WO00/13682, WO01/02409, WO99/26627, WO01/40230, WO00/24742, WO98/42711, WO00/17201, WO03/022283 and the like. These compounds can be obtained by the methods of production described in the above-mentioned documents.

Examples of the pharmaceutically acceptable salt of the compound having an adenosine $A_{2A}$ receptor antagonistic activity include pharmaceutically acceptable acid addition salts, metal salts, ammonium salts, organic amine addition salts, amino acid addition salts and the like.

Examples of the pharmaceutically acceptable acid addition salts include an inorganic acid salt such as hydrochloride, sulfate and phosphate; and an organic acid salt such as acetate, maleate, fumarate, tartrate, citrate and methanesulfonate. Examples of the pharmaceutically acceptable metal salts include an alkali metal salt such as sodium salt and potassium salt; alkaline earth metal salt such as magnesium salt and calcium salt; aluminum salt; zinc salt and the like. Examples of the pharmaceutically acceptable ammonium salts include ammonium and tetramethylammonium. Examples of the pharmaceutically acceptable organic amine addition salt include an addition salt of morpholine or piperidine. Examples of the pharmaceutically acceptable amino acid addition salts include an addition salt of lysine, glycine or phenylalanine. When it is desired to obtain a salt of the compound having an adenosine $A_{2A}$ receptor antagonistic activity, in instances in which the compound is obtained in the form of a salt, the product may be directly purified. Alternatively, in instances in which the compound is obtained in the form of a free base, the product may be dissolved or suspended in a suitable solvent, followed by addition of an acid or a base to form a salt.

Examples of the antidepressant drug include tricyclic antidepressants, tetracyclic antidepressants, selective serotonin reuptake inhibitors (SSRI), selective noradrenalin reuptake inhibitors (Selective Norepinephrine Reuptake Inhibitor), serotonin-noradrenalin reuptake inhibitors (Serotonin-Norepinephrine Reuptake Inhibitor; SNRI), dopamine reuptake inhibitors, monoamine oxidase (MAO) inhibitors, 5-HT$_2$ antagonists and the like. These may be used alone or in combination, as long as it is not contraindicated, for the pharmaceutical composition, the therapeutic agent for depression, the kit, the kit for treatment of depression or the method for treating depression of the present invention.

Examples of the tricyclic antidepressant include imipramine, clomipramine, amitriptyline, nortriptyline, amoxapine, trimipramine, lofepramine, dosulepin, protriptyline, doxepin, desipramine, pharmaceutically acceptable salts thereof (examples of the pharmaceutically acceptable salts include the salts illustrated as the pharmaceutically acceptable salts of the above-mentioned Compound (I)) and the like. Those may be in the form of a hydrate or the like. Among them, imipramine hydrochloride, clomipramine hydrochloride, amitriptyline hydrochloride, nortriptyline hydrochloride, amoxapine, trimipramine maleate, lofepramine, lofepramine hydrochloride, dosulepin hydrochloride, protriptyline, doxepin or desipramine hydrochloride is preferred.

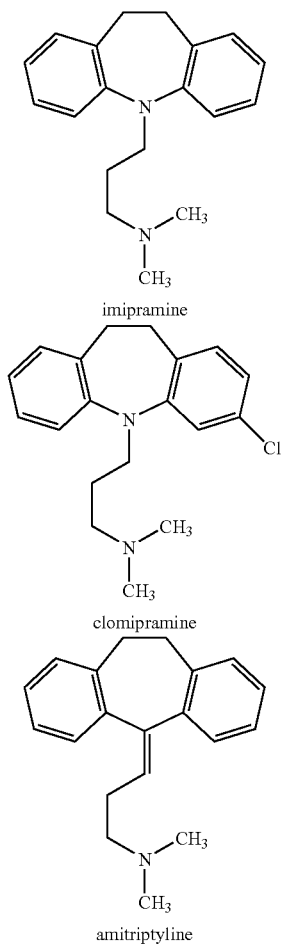

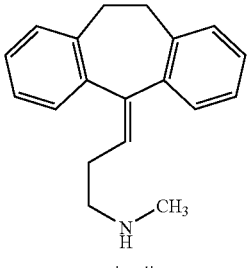

nortriptyline

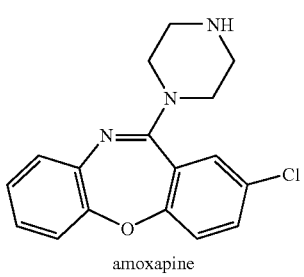

amoxapine

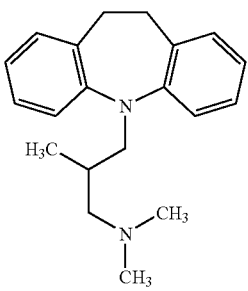

trimipramine

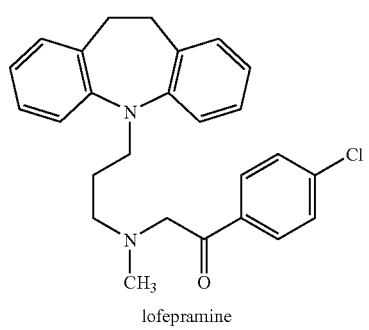

lofepramine

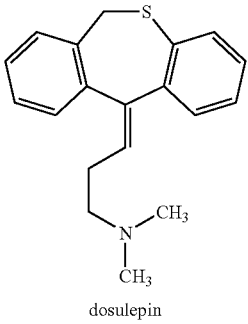

dosulepin

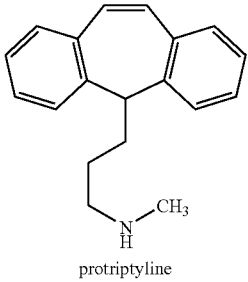

protriptyline

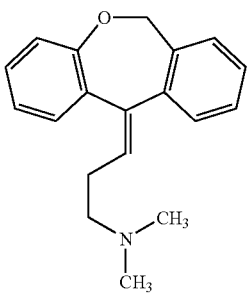

doxepin

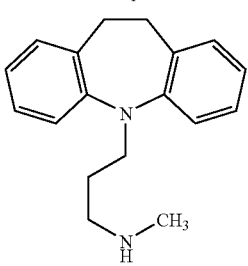

desipramine

Examples of the tetracyclic antidepressant include maprotiline, mianserin, setiptiline, pharmaceutically acceptable salts thereof (examples of the pharmaceutically acceptable salt include the salts illustrated as the pharmaceutically acceptable salts of the above-mentioned Compound (I)) and the like. Those may be in the form of a hydrate or the like. Among them, maprotiline hydrochloride, mianserin hydrochloride or setiptiline maleate is preferred.

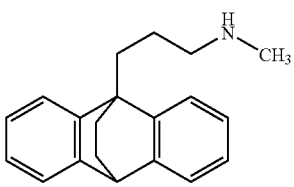

maprotiline

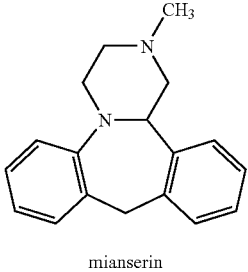

mianserin

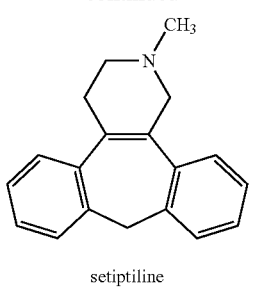

setiptiline

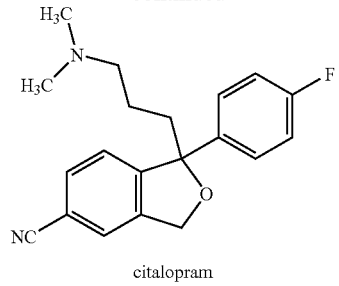

citalopram

The selective serotonin reuptake inhibitor is not particularly limited, as long as it selectively inhibits reuptake of serotonin, and examples thereof include fluoxetine, sertraline, paroxetine, citalopram, fluvoxamine, trazodone, nefazodone, pharmaceutically acceptable salts thereof (examples of the pharmaceutically acceptable salt include the salts illustrated as the pharmaceutically acceptable salts of the above-mentioned Compound (I)) and the like. Those may be in the form of a hydrate or the like. Among them, fluoxetine hydrochloride, sertraline hydrochloride, paroxetine hydrochloride, paroxetine hydrochloride hydrate, citalopram hydrobromide, fluvoxamine maleate, trazodone hydrochloride or nefazodone hydrochloride is preferred.

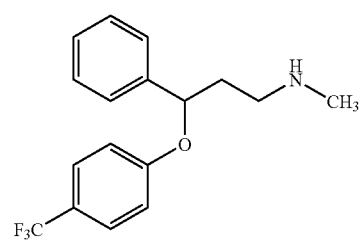

fluoxetine

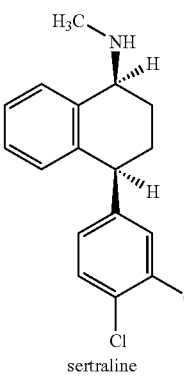

sertraline

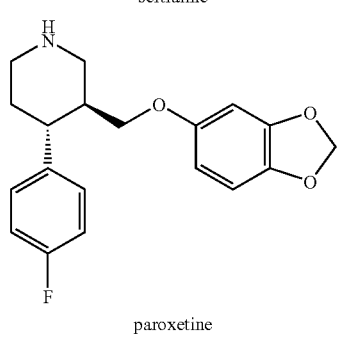

paroxetine

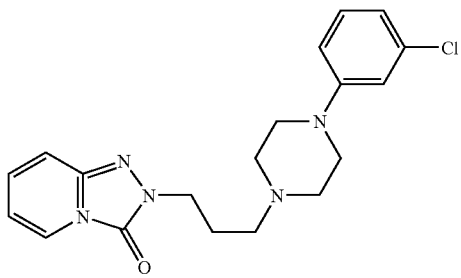

fluvoxamine trazodone

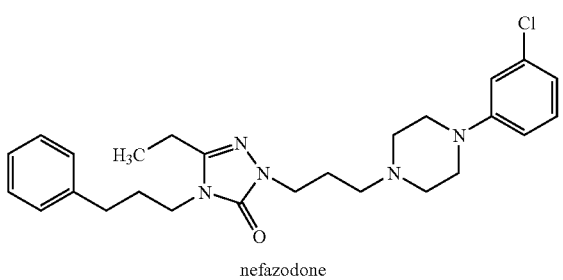

nefazodone

The selective noradrenalin reuptake inhibitor is not particularly limited, as long as it selectively inhibits reuptake of noradrenalin, and examples thereof include reboxetine, mirtazapine, maprotiline, nortriptyline, amoxapine, bupropion, pharmaceutically acceptable salts thereof (examples of the pharmaceutically acceptable salt include the salts illustrated as the pharmaceutically acceptable salts of the above-mentioned Compound (I)) and the like. Those may be in the form of a hydrate or the like. Among them, reboxetine mesylate, mirtazapine, maprotiline hydrochloride, nortriptyline hydrochloride, amoxapine, bupropion or bupropion hydrochloride is preferred.

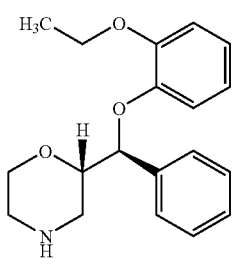
reboxetine

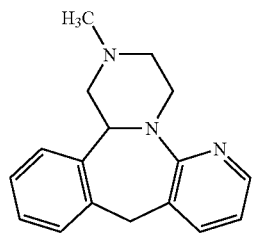
mirtazapine

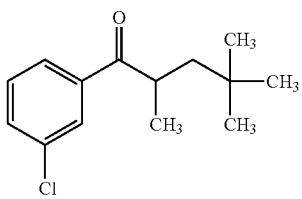
bupropion

The serotonin-noradrenalin reuptake inhibitor is not particularly limited, as long as it selectively inhibits reuptake of serotonin and noradrenalin, and examples thereof include milnacipran, venlafaxine, duloxetine, pharmaceutically acceptable salts thereof (examples of the pharmaceutically acceptable salt include the salts illustrated as the pharmaceutically acceptable salts of the above-mentioned Compound (I)) and the like. Those may be in the form of a hydrate or the like. Among them, milnacipran hydrochloride, venlafaxine hydrochloride or duloxetine hydrochloride is preferred.

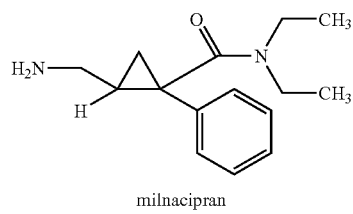
milnacipran

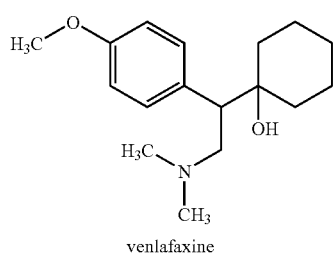
venlafaxine

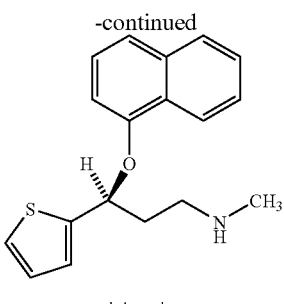
duloxetine

The dopamine reuptake inhibitor is not particularly limited, as long as it inhibits reuptake of dopamine, and examples thereof include venlafaxine, pharmaceutically acceptable salts thereof (examples of the pharmaceutically acceptable salt include the salts illustrated as the pharmaceutically acceptable salts of the above-mentioned Compound (I)) and the like. Those may be in the form of a hydrate or the like. Among them, venlafaxine hydrochloride is preferred.

The MAO inhibitor is not particularly limited, as long as it increases intracerebral amount of a biogenic amine (e.g., adrenaline, noradrenalin and serotonin) through inhibiting monoamine oxidase, and examples thereof include e.g., selegiline, safinamide, moclobemide, phenelzine, isocarboxazid, tranylcypromine, and pharmaceutically acceptable salts thereof (examples of the pharmaceutically acceptable salt include the salts illustrated as the pharmaceutically acceptable salts of the above-mentioned Compound (I)) and the like. Those may be in the form of a hydrate or the like. Among them, selegiline hydrochloride, safinamide mesylate or moclobemide is preferred.

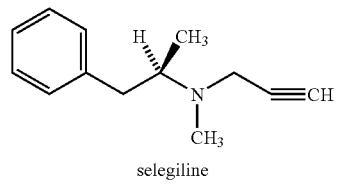
selegiline

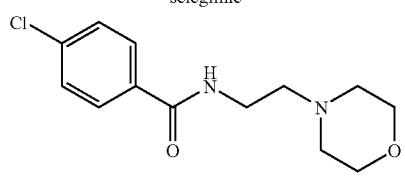
mociobemide

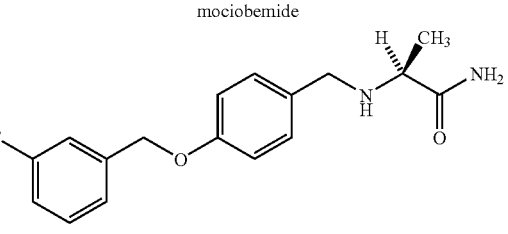
safinamide

Examples of the 5-HT$_2$ antagonist include mirtazapine, trazodone, nefazodone, and pharmaceutically acceptable salts thereof (examples of the pharmaceutically acceptable salt include the salts illustrated as the pharmaceutically acceptable salts of the above-mentioned Compound (I)) and the like. Those may be in the form of a hydrate or the like.

Among them, mirtazapine, trazodone hydrochloride or nefazodone hydrochloride is preferred.

The pharmaceutical composition of the present invention can be used for treatment and/or prevention of, for example, Psychiatric disorders such as depression.

Compound (I) or a pharmaceutically acceptable salt thereof and an antidepressant drug, which are used in the pharmaceutical composition or the therapeutic agent for depression of the present invention, or the compound having an adenosine $A_{2A}$ receptor antagonistic activity or a pharmaceutically acceptable salt thereof and a monoamine oxidase inhibitor, which are used in the therapeutic agent for depression of the present invention, can be used or administered either as a single formulation (combined formulation) or as a combination of several formulations, as long as both of these active ingredients are formulated into formulations, respectively. Among them, combination of two or more formulations is preferred. Preferably, these formulations are used in a dosage form of, for example, a tablet, an injection or the like. In using or administrating as a combination of several formulations, these formulations may be used or administered simultaneously or separately at a time interval.

In using or administrating separately at a time interval, the time interval may be provided according to characteristics of the formulations to be combined (the onset time of the activity, peak of occurrence of the action, and the like). Although the interval, and the order of use or administration are not particularly limited, they may be used or administered, for example, at an interval of 5 minutes to 72 hours, preferably 30 minutes to 30 hours.

Compound (I) or a pharmacologically acceptable salt thereof and the antidepressant drug are combined, in which the combination ratio of the antidepressant drug is, for example, between 0.0001 to 1000 wt %, preferably between 0.001 to 500 wt %, and more preferably between 0.005 to 300 wt % of Compound (I) or a pharmaceutically acceptable salt thereof.

The compound having an adenosine $A_{2A}$ receptor antagonistic activity or a pharmaceutically acceptable salt thereof and the monoamine oxidase inhibitor are combined, in which the combination ratio of the monoamine oxidase inhibitor, for example, between 0.0001 to 1000 wt %, preferably between 0.001 to 500 wt %, more preferably between 0.005 to 300 wt %, and still more preferably between 0.01 to 200 wt % of the compound having an adenosine $A_{2A}$ receptor antagonistic activity or a pharmaceutically acceptable salt thereof.

In administrating as a combination of several formulations, for example, a first component (a) containing Compound (I) or a pharmaceutically acceptable salt thereof and a second component (b) containing the antidepressant drug; or a first component (a) containing the compound having an adenosine $A_{2A}$ receptor antagonistic activity or a pharmaceutically acceptable salt thereof and a second component (b) containing the monoamine oxidase inhibitor are independently formulated as described above to make a kit, and then by using this kit, each component can be administered simultaneously or separately at a time interval to the same subject, via the same route or via different routes.

Examples of the kit include those which comprise the content and two or more containers (e.g., vial, bag or the like), which are not particularly limited in material, shape and the like, as long as they do not cause denaturation of the components, which are the contents, due to external temperature or light on storage, elution of chemical ingredients from the container, and the like, and that are in a form to enable to administer the above first component and the second component, which are the contents via separate routes (e.g., tube or the like) or via the same route. Specifically, examples of the kit include the kit in the dosage form of a tablet, an injection and the like.

Furthermore, the method for treating depression of the present invention can be performed in a manner similar to that in the method of using or administering Compound (I) or the compound having an adenosine $A_{2A}$ receptor antagonistic activity, or a pharmaceutically acceptable salt thereof, and the antidepressant drug, which are used in the pharmaceutical composition or the therapeutic agent for depression as described above. More specifically, it can be carried out by independently formulating Compound (I) or the compound having an adenosine $A_{2A}$ receptor antagonistic activity, or a pharmaceutically acceptable salt thereof, and the antidepressant drug, as long as both of these active ingredients is formulated, respectively, and administering, for example, either as a single formulation or as a combination of several formulations, preferably as a combination of two or more formulations. In administrating as a combination of several formulations, these formulations can be administered simultaneously or separately at a time interval, and they can be also administered by using the kit as described above.

Next, therapeutic effects for depression by the combined use of Compound (I) or a pharmaceutically acceptable salt thereof and the antidepressant drug are more specifically explained by Test Examples.

TEST EXAMPLE 1

Forced Swimming Method in Mice

The test was carried out with reference to the method of Porsolt et al., [Arch. Int. Pharmacodyn. Ther., 229, 327-336 (1977)], which is an animal model of depression.

Experiment was conducted using 10 ddY male mice (weighing 20 to 35 g, Nihon SLC Co., Ltd) per one group.

An acrylic transparent cylinder having a diameter of 10 cm and a height of 25 cm was filled with water having a temperature of about 24° C. Height from the bottom of the cylinder to the surface of the water was adjusted to be about 9 cm.

The mice were forced to swim individually for a period of 6 minutes, the total duration of immobility during the last 4 minutes of 6 minutes test was measured (significance test: Dunnett test).

The antidepressant drug and Compound (I) were suspended in distilled water for injection (manufactured by Otsuka Pharmaceutical Co., Ltd.) containing 0.5% MC (methyl cellulose), respectively, for use in the test. Time point of administration of the antidepressant drug was predetermined such that the peak of onset of activity by the antidepressant drug overlaps with the peak of onset of activity by Compound (I). According to the predetermined time, the suspension containing the antidepressant drug was orally administered to a group administered the antidepressant drug alone or a group administered the antidepressant drug and Compound (I) in combination (0.1 mL per 10 g of the mouse body weight). Further, the suspension containing Compound (I) was orally administered to the group administered the antidepressant drug and Compound (I) in combination, 1 hour before the test (0.1 mL per 10 g of the mouse body weight). A solution without containing a test compound [distilled water for injection (manufactured by Otsuka Pharmaceutical Co., Ltd.) containing 0.5% MC] and the suspension containing Compound (I) were orally administered to a solvent control group and to a group administered Compound (I) alone, 1 hour before the test, respectively (0.1 mL per 10 g of the mouse body weight).

Effect obtained by combining Compound (I) and the antidepressant drug was evaluated according to the following index.

The duration of Immobility in the solvent control group was assumed to be 100%, and each rate of change (%) of the duration of immobility in the above administration group to the duration of immobility in the solvent control group was calculated, and was compared. The duration of immobility in each administration group, and the rate of change (%) of the duration of immobility are shown in Table 1.

TABLE 1

| Test compound (dose: mg/kg) | Duration of immobility (sec) | |
|---|---|---|
| | Mean value ± Standard error | Rate of change of duration of immobility to solvent control group (%) |
| Solvent control group | 196.5 ± 12.0 | — |
| Compound (I) (0.08) | 155.6 ± 13.3* | −21 |
| Venlafaxine hydrochloride (5.00) | 173.1 ± 20.7* | −12 |
| Compound (I) (0.08) + Venlafaxine hydrochloride (5.00) | 118.2 ± 17.4** | −40 |

*Not Significant,
**p < 0.01.

TEST EXAMPLE 2

Mouse Tail Suspension Method

The test was carried out with reference to the method of Steru et al., [Psychopharmacol., 85, 367-370 (1985)], which is an animal model of depression.

Experiment was conducted using 10 ICR male mice (weighing 20 to 35 g, Nihon SLC Co., Ltd) per one group.

An acrylic or metallic bar was fixed horizontally such that height of about 60 cm from the floor face is provided.

The mouse was suspended at a site of about 2 cm from the tip of the tail, from the bar for a period of 6 minutes. Duration of immobility during the last 4 minutes of 6 minutes test was measured (significance test: Student's t test). For fixing the mouse, an adhesive tape was used.

The antidepressant drug and Compound (I) were suspended in distilled water for injection (manufactured by Otsuka Pharmaceutical Co., Ltd.) containing 0.5% MC (methyl cellulose), respectively, for use in the test. Time point of administration of the antidepressant drug was predetermined such that the peak of onset of activity by the antidepressant drug overlaps with the peak of onset of activity by Compound (I). According to the predetermined time, the suspension containing the antidepressant drug was orally administered to a group administered the antidepressant drug alone or a group administered the antidepressant drug and Compound (I) in combination (0.1 mL per 10 g of the mouse body weight). Further, the suspension containing Compound (I) was orally administered to the group administered the antidepressant drug and Compound (I) in combination, 1 hour before the test (0.1 mL per 10 g of the mouse body weight). A solution without containing a test compound [distilled water for injection (manufactured by Otsuka Pharmaceutical Co., Ltd.) containing 0.5% MC] and the suspension containing Compound (I) were orally administered to a solvent control group and to a group administered Compound (I) alone, 1 hour before the test, respectively (0.1 mL per 10 g of the mouse body weight).

Effect obtained by combining Compound (I) and the antidepressant drug was evaluated according to the following index.

The duration of Immobility in the solvent control group was assumed to be 100%, and each rate of change (%) of the duration of immobility in the above administration group to the duration of immobility in the solvent control group was calculated, and was compared. The duration of immobility in each administration group, and the rate of change (%) of the duration of immobility are shown in Table 2 and Table 3.

TABLE 2

| Test compound (dose: mg/kg) | Duration of immobility (sec) | |
|---|---|---|
| | Mean value ± Standard error | Rate of change of duration of immobility to solvent control group (%) |
| Solvent control group | 81.3 ± 13.1 | — |
| Compound (I) (0.04) | 70.1 ± 19.1* | −14 |
| Paroxetine hydrochloride hydrate (2.50) | 79.6 ± 16.6* | −2 |
| Compound (I) (0.04) + Paroxetine hydrochloride hydrate (2.50) | 31.7 ± 9.6** | −61 |

*Not Significant,
**p < 0.01

TABLE 3

| Test compound (dose: mg/kg) | Duration of immobility (sec) | |
|---|---|---|
| | Mean value ± Standard error | Rate of change of duration of immobility to solvent control group (%) |
| Solvent control group | 102.2 ± 9.1 | — |
| Compound (I) (0.04) | 87.9 ± 14.9* | −26 |
| Fluoxetine hydrochloride (10.00) | 85.7 ± 18.9* | −16 |
| Compound (I) (0.04) + Fluoxetine hydrochloride (10.00) | 40.5 ± 14.3** | −60 |

*Not Significant,
**p < 0.01

From the results in Test Examples 1 and 2, it was found that the duration of immobility decrease drastically by administering Compound (I) and an antidepressant drug in combination, in comparison with administering an antidepressant drug or Compound (I) alone. In other words, it is believed that the use of Compound (I) or a pharmaceutically acceptable salt thereof and an antidepressant drug in combination enables more effective treatment of depression.

As described hereinabove, the pharmaceutical composition of the present invention can be used, administered or produced as a single formulation or as a combination of several formulations, as long as active ingredients, which is Compound (I) or a pharmaceutically acceptable salt thereof and an antidepressant drug, or a compound having an adenosine $A_{2A}$ receptor antagonistic action or a pharmaceutically acceptable salt thereof and a monoamine oxidase inhibitor, are formulated into formulations, respectively. It is desired that these pharmaceutical compositions are in a single dosage form which is suited for oral administration or parenteral administration such as injection or the like. Moreover, in using or administrating as a combination of several formulations, these formulations can be used or administrated simultaneously or separately at a time interval.

These formulations can be produced by a common method using pharmaceutically acceptable diluent, excipient, disintegrant, lubricant, binder, surfactant, water, physiological saline, vegetable oil solubilizer, isotonizing agent, preservative, anti-oxidizing agent and the like in addition to the active ingredient, respectively.

Upon preparation of a tablet, for example, an excipient such as lactose, a disintegrant such as starch, a lubricant such as magnesium stearate, a binder such as hydroxypropyl cellulose, a surfactant such as a fatty acid ester, a plasticizer such as glycerin, and the like may be used according to a common method.

Upon preparation of an injection, water, physiological saline, vegetable oil, a solvent, a solubilizer, an isotonizing agent, a preservative, an anti-oxidizing agent and the like may be used according to a common method.

When Compound (I) or a pharmaceutically acceptable salt thereof and an antidepressant drug, or a compound having an adenosine $A_{2A}$ receptor antagonistic activity or a pharmaceutically acceptable salt thereof and a monoamine oxidase inhibitor are used or administered as a combination of several formulations, respectively, with the object described above, it is preferred that Compound (I) or a pharmaceutically acceptable salt thereof and the antidepressant drug, or the compound having an adenosine $A_{2A}$ receptor antagonistic action or a pharmaceutically acceptable salt thereof and the monoamine oxidase inhibitor are usually administered in the following dose per day, although each dose and frequency of administration may vary depending on the dosage form, age, weight and symptoms of the patient, and the like.

When administered orally, for example, as a tablet, the Compound (I) or a pharmaceutically acceptable salt thereof and the antidepressant drug, or the compound having an adenosine $A_{2A}$ receptor antagonistic action or a pharmaceutically acceptable salt thereof and the monoamine oxidase inhibitor are usually administered simultaneously or separately at a time interval, in an amount of 0.0001 to 50 mg/kg and 0.001 to 1000 mg/kg, preferably 0.001 to 30 mg/kg and 0.005 to 100 mg/kg, and more preferably 0.005 to 20 mg/kg and 0.01 to 50 mg/kg per day, respectively, once or in several times.

When administered parenterally, for example, as an injection, Compound (I) or a pharmaceutically acceptable salt thereof and the antidepressant drug, or the compound having an adenosine $A_{2A}$ receptor antagonistic action or a pharmaceutically acceptable salt thereof and the monoamine oxidase inhibitor are usually administered simultaneously or separately with a time interval, in an amount of 0.0001 to 50 mg/kg and 0.0005 to 500 mg/kg, preferably 0.0005 to 20 mg/kg and 0.005 to 100 mg/kg, and more preferably 0.001 to 15 mg/kg and 0.03 to 30 mg/kg per day, respectively, once or in several times.

Furthermore, when Compound (I) or a pharmaceutically acceptable salt thereof and an antidepressant drug, or a compound having an adenosine $A_{2A}$ receptor antagonistic action or a pharmaceutically acceptable salt thereof and a monoamine oxidase inhibitor are used or administered as a single formulation with the object described above, it is preferred that preparation is conducted as a single formulation to give each dose as in the case of use or administration as a combination of multiple formulations described above, followed by use or administration, although each dose and frequency of administration may vary depending on the dosage form, age, weight and symptoms of the patient, and the like.

Mode of the present invention is explained below by way of Examples, however, scope of the invention is not limited by these Examples.

BEST MODE FOR CARRYING OUT THE INVENTION

Example 1

Tablet (Compound (I))

According to a conventional method, tablets having the following composition are prepared. Compound (I) in an amount of 40 g, 286.8 g of lactose and 60 g of potato starch are mixed, and thereto is added 120 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 20 mg of Compound (I) per tablet).

Prescription

| | |
|---|---|
| Compound (I) | 20 mg |
| Lactose | 143.4 mg |
| Potato starch | 30 mg |
| Hydroxypropyl cellulose | 6 mg |
| Magnesium stearate | 0.6 mg |
| | 200 mg |

Example 2

Tablet (Imipramine Hydrochloride)

According to a conventional method, tablets having the following composition are prepared. Imipramine hydrochloride in an amount of 50 g, 276.8 g of lactose and 60 g of potato starch are mixed, and thereto is added 120 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 25 mg of imipramine hydrochloride per tablet).

Prescription

| | |
|---|---|
| Imipramine hydrochloride | 25 mg |
| Lactose | 138.4 mg |
| Potato starch | 30 mg |
| Hydroxypropyl cellulose | 6 mg |
| Magnesium stearate | 0.6 mg |
| | 200 mg |

Example 3

Tablet (Compound (I) and Selegiline Hydrochloride)

According to a conventional method, tablets having the following composition are prepared. Compound (I) in an amount of 20 g, 5 g of selegiline hydrochloride, 300.8 g of lactose and 61 g of potato starch are mixed, and thereto is added 120 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 10 mg of Compound (I) and 2.5 mg of selegiline hydrochloride per tablet).

Prescription

| | |
|---|---|
| Compound (I) | 10 mg |
| Selegiline hydrochloride | 2.5 mg |
| Lactose | 150.4 mg |
| Potato starch | 30.5 mg |
| Hydroxypropyl cellulose | 6 mg |
| Magnesium stearate | 0.6 mg |
| | 200 mg |

Example 4

Tablet (Compound (I) and Mianserin Hydrochloride)

According to a conventional method, tablets having the following composition are prepared. Compound (I) in an amount of 20 g, 20 g of mianserin hydrochloride, 285.8 g of lactose and 61 g of potato starch are mixed, and thereto is added 120 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 10 mg of Compound (I) and 10 mg of mianserin hydrochloride per tablet).

Prescription

| | |
|---|---|
| Compound (I) | 10 mg |
| Mianserin hydrochloride | 10 mg |
| Lactose | 142.9 mg |
| Potato starch | 30.5 mg |
| Hydroxypropyl cellulose | 6 mg |
| Magnesium stearate | 0.6 mg |
| | 200 mg |

Example 5

Tablet (Compound (I))

According to a conventional method, tablets having the following composition are prepared. Compound (I) in an amount of 10 g, 143.4 g of lactose and 40 g of potato starch are mixed, and thereto is added 60 g of a 10% aqueous solution of hydroxypropyl cellulose. After blending, granulating and drying this mixture according to a conventional method, whole grains are prepared to give grains for tabletting. Thereto is added 0.6 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 5 mg of Compound (I) per tablet).

Prescription

| | |
|---|---|
| Compound (I) | 5 mg |
| Lactose | 71.7 mg |
| Potato starch | 20 mg |
| Hydroxypropyl cellulose | 3 mg |
| Magnesium stearate | 0.3 mg |
| | 100 mg |

Example 6

Tablet (Fluoxetine Hydrochloride)

According to a conventional method, tablets having the following composition are prepared. Fluoxetine hydrochloride in an amount of 40 g, 286.8 g of lactose and 60 g of potato starch are mixed, and thereto is added 120 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 20 mg of fluoxetine hydrochloride per tablet).

Prescription

| | |
|---|---|
| Fluoxetine hydrochloride | 20 mg |
| Lactose | 143.4 mg |
| Potato starch | 30 mg |
| Hydroxypropyl cellulose | 6 mg |
| Magnesium stearate | 0.6 mg |
| | 200 mg |

Example 7

Tablet (Compound (I) and Paroxetine Hydrochloride Hydrate)

According to a conventional method, tablets having the following composition are prepared. Compound (I) in an amount of 10 g, 40 g of paroxetine hydrochloride hydrate, 275.8 g of lactose and 61 g of potato starch are mixed, and thereto is added 120 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 5 mg of Compound (I) and 20 mg of paroxetine hydrochloride hydrate per tablet).

Prescription

| Compound (I) | 5 mg |
|---|---|
| Paroxetine hydrochloride hydrate | 20 mg |
| Lactose | 137.9 mg |
| Potato starch | 30.5 mg |
| Hydroxypropyl cellulose | 6 mg |
| Magnesium stearate | 0.6 mg |
| | 200 mg |

Example 8

Tablet (Venlafaxine Hydrochloride)

According to a conventional method, tablets having the following composition are prepared. Venlafaxine hydrochloride in an amount of 100 g, 248.8 g of lactose and 40 g of potato starch are mixed, and thereto is added 100 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 50 mg of venlafaxine hydrochloride per tablet).
Prescription

| Venlafaxine hydrochloride | 50 mg |
|---|---|
| Lactose | 124.4 mg |
| Potato starch | 20 mg |
| Hydroxypropyl cellulose | 5 mg |
| Magnesium stearate | 0.6 mg |
| | 200 mg |

Example 9

Tablet (Compound (I) and Milnacipran Hydrochloride)

According to a conventional method, tablets having the following composition are prepared. Compound (I) in an amount of 10 g, 30 g of milnacipran hydrochloride, 285.8 g of lactose and 61 g of potato starch are mixed, and thereto is added 120 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 5 mg of Compound (I) and 15 mg of milnacipran hydrochloride per tablet).
Prescription

| Compound (I) | 5 mg |
|---|---|
| Milnacipran hydrochloride | 15 mg |
| Lactose | 142.9 mg |
| Potato starch | 30.5 mg |
| Hydroxypropyl cellulose | 6 mg |
| Magnesium stearate | 0.6 mg |
| | 200 mg |

Example 10

Injection (Compound (I))

According to a conventional method, injections having the following composition are prepared. Compound (I) in an amount of 0.5 g is dissolved in 100 g of purified soybean oil, and thereto are added 12 g of purified yolk lecithin and 25 g of glycerin for injection. This mixture is adjusted to give 1000 mL with distilled water for injection followed by blending emulsification according to a conventional method. Thus resulting dispersion liquid is subjected to aseptic filtration using a 0.2 μm disposable type membrane filter. Thereafter, each 2 mL of the liquid is aseptically filled in a glass vial to obtain injections (containing 1 mg of Compound (I) per vial).
Prescription

| Compound (I) | 1 mg |
|---|---|
| Purified soybean oil | 200 mg |
| Purified yolk lecithin | 24 mg |
| Glycerin for injection | 50 mg |
| Distilled water for injection | 1.72 mL |
| | 2.00 mL |

Example 11

Injection (Bupropion)

According to a conventional method, injections having the following composition are prepared. Bupropion in an amount of 5 g is dissolved in 100 g of purified soybean oil, and thereto are added 12 g of purified yolk lecithin and 25 g of glycerin for injection. This mixture is adjusted to give 1000 mL with distilled water for injection followed by blending emulsification according to a conventional method. Thus resulting dispersion liquid is subjected to aseptic filtration using a 0.2 μm disposable type membrane filter. Thereafter, each 2 mL of the liquid is aseptically filled in a glass vial to obtain injections (containing 10 mg of bupropion per vial).
Prescription

| Bupropion | 10 mg |
|---|---|
| Purified soybean oil | 200 mg |
| Purified yolk lecithin | 24 mg |
| Glycerin for injection | 50 mg |
| Distilled water for injection | 1.72 mL |
| | 2.00 mL |

Example 12

Injection (Compound (I) and Clomipramine Hydrochloride)

According to a conventional method, injections having the following composition are prepared. Compound (I) in an amount of 1 g and 12.5 g of clomipramine hydrochloride are dissolved in 100 g of purified soybean oil, and thereto are added 12 g of purified yolk lecithin and 25 g of glycerin for injection. This mixture is adjusted to give 1000 mL with distilled water for injection followed by blending emulsification according to a conventional method. Thus resulting dispersion liquid is subjected to aseptic filtration using a 0.2 μm disposable type membrane filter. Thereafter, each 2 mL of the liquid is aseptically filled in a glass vial to obtain injections (containing 2 mg of Compound (I) and 25 mg of clomipramine hydrochloride per vial).
Prescription

| | |
|---|---|
| Compound (I) | 2 mg |
| Clomipramine hydrochloride | 25 mg |
| Purified soybean oil | 200 mg |
| Purified yolk lecithin | 24 mg |
| Glycerin for injection | 50 mg |
| Distilled water for injection | 1.62 mL |
| | 2.00 mL |

Example 13

Tablet (Nefazodone Hydrochloride)

According to a conventional method, tablets having the following composition are prepared. Nefazodone hydrochloride in an amount of 100 g, 248.8 g of lactose and 40 g of potato starch are mixed, and thereto is added 100 g of a 10% aqueous solution of hydroxypropyl cellulose. After blending, granulating and drying this mixture according to a conventional method, whole grains are prepared to give grains for tabletting. Thereto is added 1.2 g of magnesium stearate followed by mixing. Tabletting is carried out with a tabletting machine having a pestle with a diameter of 8 mm (manufactured by KIKUSUI SEISAKUSHO LTD., type RT-15) to obtain tablets (containing 50 mg of nefazodone hydrochloride per tablet).
Prescription

| | |
|---|---|
| Nefazodone hydrochloride | 50 mg |
| Lactose | 124.4 mg |
| Potato starch | 20 mg |
| Hydroxypropyl cellulose | 5 mg |
| Magnesium stearate | 0.6 mg |
| | 200 mg |

INDUSTRIAL APPLICABILITY

The present invention provide pharmaceutical compositions which comprises (E)-8-(3,4-dimethoxystyryl)-1,3-diethyl-7-methyl-3,7-dihydro-1H-purine-2,6-dione or a pharmaceutically acceptable salt thereof and an antidepressant drug, and the like.

The invention claimed is:
1. An orally administered pharmaceutical composition, comprising:
(a) (E)-8-(3,4-dimethoxystyryl)-1,3-diethyl-7-methyl-3,7-dihydro-1H-purine-2,6-dione represented by the formula (I):

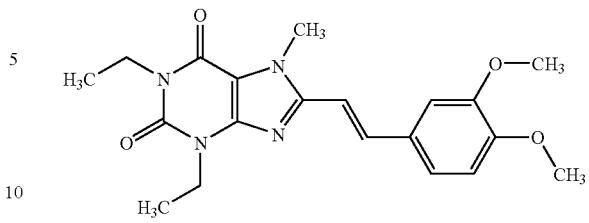

or a pharmaceutically acceptable salt thereof, and
(b) a selective serotonin reuptake inhibitor selected from the group consisting of paroxetine or a pharmaceutically acceptable salt and/or hydrate thereof, and fluoxetine or a pharmaceutically acceptable salt and/or hydrate thereof,
wherein a dose of said composition provides 0.0001-50 mg/kg of said (E)-8-(3,4-dimethoxystyryl)-1,3-diethyl-7-methyl-3,7-dihydro-1H-purine-2,6-dione or said pharmaceutically acceptable salt thereof, and 0.001-1000 mg/kg of said serotonin reuptake inhibitor.

2. The pharmaceutical composition according to claim 1, wherein the pharmaceutically acceptable salt of paroxetine or fluoxetine, is a hydrochloride.

3. The pharmaceutical composition according to claim 1, wherein the selective serotonin reuptake inhibitor is fluoxetine hydrochloride, paroxetine hydrochloride, or paroxetine hydrochloride hydrate.

4. The pharmaceutical composition according to claim 1, wherein a dose of said composition provides 0.001 to 30 mg/kg of said (E)-8-(3,4-dimethoxystyryl)-1,3-diethyl-7-methyl-3,7-dihydro-1H-purine-2,6-dione, or said pharmaceutically acceptable salt thereof, and 0.005 to 1000 mg/kg of said serotonin reuptake inhibitor.

5. The pharmaceutical composition according to claim 4, wherein the pharmaceutically acceptable salt of paroxetine or fluoxetine, is a hydrochloride.

6. The pharmaceutical composition according to claim 4, wherein the serotonin reuptake inhibitor is fluoxetine hydrochloride, paroxetine hydrochloride, or paroxetine hydrochloride hydrate.

7. The pharmaceutical composition according to claim 1, wherein a dose of said composition provides 0.005 to 20 mg/kg of said (E)-8-(3,4-dimethoxystyryl)-1,3-diethyl-7-methyl-3,7-dihydro-1H-purine-2,6-dione, or said pharmaceutically acceptable salt thereof, and 0.01 to 50 mg/kg of said serotonin reuptake inhibitor.

8. The pharmaceutical composition according to claim 7, wherein the pharmaceutically acceptable salt of paroxetine or fluoxetine, is a hydrochloride.

9. The pharmaceutical composition according to claim 7, wherein the serotonin reuptake inhibitor is fluoxetine hydrochloride, paroxetine hydrochloride, or paroxetine hydrochloride hydrate.

* * * * *

UNITED STATES PATENT AND TRADEMARK OFFICE
CERTIFICATE OF CORRECTION

| | |
|---|---|
| PATENT NO. | : 8,034,820 B2 |
| APPLICATION NO. | : 10/565239 |
| DATED | : October 11, 2011 |
| INVENTOR(S) | : Hiroshi Kase et al. |

It is certified that error appears in the above-identified patent and that said Letters Patent is hereby corrected as shown below:

ON THE TITLE PAGE [57] ABSTRACT:

Line 3, "comprises" should read --comprise--.

COLUMN 1:

Line 21, "a treatment" should read --treatment-- and
          "carried out" should read --is carried out--;
    Line 35, "38," should read --38,--; and
    Line 40, "38," should read --38,--.

COLUMN 3:

Line 36, "drug for" should read --drug ¶ for-- (full margin).

COLUMN 4:

Line 60, "a serotonin" should read --serotonin--.

COLUMN 5:

Line 57, "thyl-3,17-dihydro-" should read --thyl-3,7-dihydro- --; and
    Line 66, "(52). The" should read --(52) The--.

COLUMN 9:
    Line 32, "inhibitor simultaneously" should read --inhibitor ¶ simultaneously-- (full
          margin); and
    Line 56, "drug for" should read --drug ¶ for-- (full margin).

Signed and Sealed this
Seventh Day of February, 2012

David J. Kappos
*Director of the United States Patent and Trademark Office*

CERTIFICATE OF CORRECTION (continued)
U.S. Pat. No. 8,034,820 B2

COLUMN 11:

Line 6, "Pubilished" should read --Published--.

COLUMN 18:

Line 50, "mociobemide" should read --moclobemide--.

COLUMN 19:

Line 5, "Psychiatric" should read --psychiatric--.

COLUMN 21:

Line 4, "Immobility" should read --immobility--.

COLUMN 22:

Line 6, "Immobility" should read --immobility--; and
    Line 54, "decrease" should read --decreases--.

COLUMN 25:

Line 18, "Prescription" should be moved to following table, as title; and
    Line 47, "Prescription" should be moved to following table, as title.

COLUMN 26:

Line 9, "Prescription" should be moved to following table, as title;
    Line 37, "Prescription" should be moved to following table, as title; and
    Line 67, "Prescription" should be moved to following table, as title.

COLUMN 27:

Line 28, "Prescription" should be moved to following table, as title; and
    Line 56, "Prescription" should be moved to following table, as title.

COLUMN 28:

Line 10, "blending" should read --blending and--; and
    Line 16, "Prescription" should be moved to following table, as title;

Ex. 10 Table,

"
| Compound (I) | 1 mg |
|---|---|
| Purified soybean oil | 200 mg |
| Purified yolk lecithin | 24 mg |
| Glycerin for injection | 50 mg |
| Distilled water for injection | 1.72 mL |
| | 2.00 mL |
"

should read

--
| Compound (I) | 1 mg |
|---|---|
| Purified soybean oil | 200 mg |
| Purified yolk lecithin | 24 mg |
| Glycerin for injection | 50 mg |
| Distilled water for injection | 1.72 mL |
| | 2.00 mL |

--;

Line 36, "blending" should read --blending and--;
Line 42, "Prescription" should be moved to following table, as title;
Ex. 11 Table, "
| Bupropion | 10 mg |
|---|---|
| Purified soybean oil | 200 mg |
| Purified yolk lecithin | 24 mg |
| Glycerin for injection | 50 mg |
| Distilled water for injection | 1.72 mL |
| | 2.00 mL |
"

should read

--
| Bupropion | 10 mg |
|---|---|
| Purified soybean oil | 200 mg |
| Purified yolk lecithin | 24 mg |
| Glycerin for injection | 50 mg |
| Distilled water for injection | 1.72 mL |
| | 2.00 mL |

--; and

Line 64, "blending" should read --blending and--.

COLUMN 29:

Line 4, "Prescription" should be moved to following table, as title;
Ex. 12, Table,

"

| Compound (I) | 2 mg |
|---|---|
| Clomipramine hydrochloride | 25 mg |
| Purified soybean oil | 200 mg |
| Purified yolk lecithin | 24 mg |
| Glycerin for injection | 50 mg |
| Distilled water for injection | 1.62 mL |
| | 2.00 mL |

"

should read

--

| Compound (I) | 2 mg |
|---|---|
| Clomipramine hydrochloride | 25 mg |
| Purified soybean oil | 200 mg |
| Purified yolk lecithin | 24 mg |
| Glycerin for injection | 50 mg |
| Distilled water for injection | 1.62 mL |
| | 2.00 mL |

--;

Line 32, "Prescription" should be moved to following table, as title; and
Line 46, "provide" should read --provides--.

COLUMN 30:

Line 25, "fluoxetine," should read --fluoxetine--;
Line 38, "fluoxetine," should read --fluoxetine--; and
Line 51, "fluoxetine," should read --fluoxetine--.